United States Patent [19]

Grollier

[11] Patent Number: 4,828,824
[45] Date of Patent: May 9, 1989

[54] DENTIFRICE CONTAINING A POLY(HYDROXYPROPYL ETHER) NON-IONIC SURFACTANT AND A SALT OF A SPECIFIC DERIVATIVE OF A PROTEIN DEGRADATION PRODUCT

[75] Inventor: Jean F. Grollier, Paris, France
[73] Assignee: L'Oreal, Paris, France
[21] Appl. No.: 95,854
[22] Filed: Sep. 14, 1987

[30] Foreign Application Priority Data

Sep. 15, 1986 [LU] Luxembourg .............. 86587

[51] Int. Cl.$^4$ .................. A61K 7/16; A61K 7/18; A61K 7/22
[52] U.S. Cl. .................. 424/52; 424/49; 424/54
[58] Field of Search .................. 424/49–58

[56] References Cited

U.S. PATENT DOCUMENTS

| | | | |
|---|---|---|---|
| 3,578,719 | 5/1971 | Kalopissis et al. | 260/611 |
| 3,821,372 | 6/1974 | Vanlerberghe | 424/170 |
| 3,928,224 | 12/1975 | Vanlerberghe | 252/172 |
| 3,929,988 | 12/1975 | Barth | 424/49 |
| 3,932,606 | 1/1976 | Barth et al. | 424/49 |
| 3,939,261 | 2/1976 | Barth | 424/49 |
| 3,966,398 | 6/1976 | Vanlerberghe | 8/11 |
| 4,071,615 | 1/1978 | Barth | 424/52 |
| 4,087,466 | 5/1978 | Vanlerberghe et al. | 260/615 B |
| 4,159,316 | 6/1979 | Januszewski et al. | 424/49 |
| 4,187,287 | 2/1980 | Schreiber et al. | 424/49 |
| 4,307,079 | 12/1981 | Zorayan et al. | 424/70 |
| 4,515,775 | 5/1985 | Vanlerberghe et al. | 424/70 |
| 4,587,120 | 5/1986 | Ozawa et al. | 424/57 |

FOREIGN PATENT DOCUMENTS 2140691 12/1984 United Kingdom .
2160098 12/1985 United Kingdom .

*Primary Examiner*—Shep K. Rose
*Attorney, Agent, or Firm*—Fleit, Jacobson, Cohn & Price

[57] ABSTRACT

Dentifrice containing, in combination, (A) a poly(hydroxypropyl ether) nonionic surfactant and (B) a salt of a specific derivative of a protein degradation product, selected from the group consisting of (i) an alkali metal salt of an N-acyl-N-methylglycine (N-acylsarcosine) of formula:

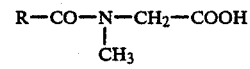

where R denotes an alkyl or a mixture of alkyls containing from 9 to 17 carbon atoms, and (ii) an alkali metal salt of a condensate of $C_{12}$–$C_{18}$ fatty acids with a hydrolyzed animal protein.

This dentifrice is characterized by good foamability and pleasant taste and does not attack the buccal mucosae and the gums.

13 Claims, No Drawings

DENTIFRICE CONTAINING A POLY(HYDROXYPROPYL ETHER) NON-IONIC SURFACTANT AND A SALT OF A SPECIFIC DERIVATIVE OF A PROTEIN DEGRADATION PRODUCT

The present invention relates to a dentifrice with improved foaming properties, without bitterness and not attacking the mucosae and the gums, containing a combination of a poly(hydroxypropyl ether) nonionic surfactant and a salt of a specific derivative of a protein degradation product chosen from the group consisting of (i) a salt of an N-acyl-N-methylglycine (N-acylsarcosine) and (ii) a salt of a condensate of copra fatty acid with a hydrolysed animal protein.

The applicant has already described, in Belgian Pat. No. 899,780, a cleaning product for tooth and mouth care and, in particular, a dentifrice which has a pleasant taste, which is not bitter and which does not attack the mucosae, this dentifrice containing a poly(hydroxypropyl ether) nonionic surfactant. This dentifrice has fairly good foamability.

However, although the foamability of the dentifrice compositions is not related to the cleaning ability, confusion appears to exist in the mind of the users and, in the case of the majority of them, the idea that a dentifrice cleans adequately only if it foams well is fairly widely held and foaming dentifrices are in greatest demand by the users.

It has therefore been found desirable to investigate a dentifrice containing a poly(hydroxypropyl ether), with improved foamability, without any bitter taste or attack on the buccal mucosa and the gums.

It is known that anionic surface-active agents have good foamability and that they are employed in dentifrices.

The most widely employed among these is sodium lauryl sulphate, which foams well but which has the disadvantage of deactivating the antimicrobial effect of the active cationic agents such as anticaries and germicidal agents, as a result of its incompatibility with these. In addition, sodium lauryl sulphate imparts a certain bitterness and attacks the buccal mucosa and the gums much more than the nonionic poly(hydroxypropyl ether) products.

Other anionic surfactants also develop a bitter taste in the mouth and attack the buccal mucosae and the gums more than the poly(hydroxypropyl ether) nonionic surfactants.

It is also known that certain amphoteric surface-active agents have good foaming properties.

Among these which are best known there may be mentioned the amphoteric surfactants sold under the trade names Miranol and, more particularly, the combination of sodium lauroamphocarboxyglycinate and sodium tridecethsulphate sold by the Miranol company under the name Miranol BT.

The subject of the invention is a dentifrice having improved foaming properties which has a pleasant taste, which is not bitter or irritant towards the buccal mucosae and the gums, and which contains, in combination, (A) a poly(hydroxypropyl ether) nonionic surface-active agent and (B) an anionic surfactant which is a salt of a specific derivative of a protein degradation product chosen from the group consisting of:

(i) a salt and preferably an alkali metal salt of an N-acyl-N-methylglycine (N-acylsarcosine) of formula:

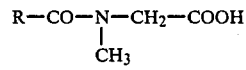

where R denotes an alkyl radical or a mixture of alkyl radicals containing from 9 to 17 carbon atoms, and (ii) a salt and preferably an alkali metal salt of a condensate of $C_{12}$–$C_{18}$ fatty acids with a hydrolysed animal protein.

Among the salts of N-acyl-N-methylglycine or N-acylsarcosine, preference is given to sodium lauroylsarcosinate of formula:

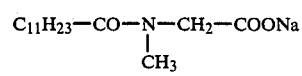

sold by the Ciba-Geigy company under the name of Sarkosyl NL 97 or NL 30, or sold by the Seppic company under the name Oramix L30.

Among the salts of condensates of fatty acids with a hydrolysed animal protein, preference is given to the potassium salt of a condensate of copra fatty acid with a hydrolysed animal protein, sold by the Grunau company under the name Lamepon S.

The poly(hydroxypropyl ether) nonionic surfactants to be employed in the dentifrice according to the invention are chosen from the compounds of formula (I) and (II) below and/or from the compounds prepared according to the process described in paragraphs (3) and (4) below:

(1) 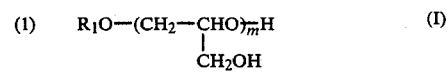 (I)

where $R_1$ denotes a radical or a mixture of alkyl radicals containing 10 to 14 carbon atoms and m is an integer or decimal from 2 to 10 and preferably from 3 to 6. These compounds of formula (I) may be prepared according to the process described in French Pat. No. 1,477,048 or in U.S. Pat. No. 3,578,719;

(2) 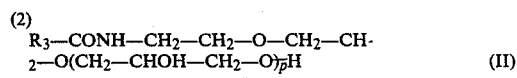 (II)

where $R_3$ denotes a radical or a mixture of alkyl and/or alkenyl radicals containing from 11 to 17 carbon atoms and p denotes an integer or decimal from 1 to 5 and preferably from 1.5 to 4. These compounds of formula (II) may be prepared according to the process described in French Pat. No. 2,328,763 or according to U.S. Pat. No. 4,307,079;

(3) compounds prepared by alkali-catalysed condensation of 2 to 10 moles and preferably of 2.5 to 6 moles of glycidol with an alpha-diol or a mixture of $C_{10}$–$C_{14}$ alpha-diols, at a temperature of 120°–180° C. and preferably from 140° to 160° C., the glycidol being added slowly, according to the process described in French Pat. No. 2,091,516 or in U.S. Pat. No. 3,821,372;

(4) compounds prepared by acid-catalysed condensation of 2 to 10 and preferably of 2.5 to 6 moles of glycidol per mole of alcohol or of alpha-diols containing 10 to 14 carbon atoms at a temperature of 50° to 120° C., the glycidol being added slowly to the alcohol or to the alpha-diol, the process for preparing these compounds being described in French Pat. No. 2,169,787 or U.S. Pat. No. 4,515,775.

The subject-matter of the patents referred to in paragraphs (1) to (4) above is incorporated by way of reference in the description of the present application.

Among the poly(hydroxypropyl ether) nonionic surfactants described in paragraphs (1), (2), (3) and (4) above, the following compounds are preferred:

$$C_{12}H_{25}O-(CH_2-\underset{\underset{CH_2OH}{|}}{CH}-O)_{\overline{4.2}}H \quad (III)$$

$$R_1O-(CH_2-\underset{\underset{CH_2OH}{|}}{CH}-O)_{\overline{3.75}}H \quad (IV)$$

where $R_1$ denotes a mixture of $C_{10}H_{21}$ and $C_{12}H_{25}$ alkyl radicals;

compounds prepared by alkali-catalysed condensation of 3.5 moles of glycidol with a mixture of alpha-diols containing from 11 to 14 carbon atoms, according to the process described in French Pat. No. 2,091,516 or in U.S. Pat. No. 3,821,372;

$$R_3-CONH-CH_2-CH_2-O-CH_2-CH_2-O-(CH_2-CHOH-CH_2-O)_{\overline{3.5}}H \quad (V)$$

where $R_3$ denotes a mixture of radicals comprising the following alkyl and alkenyl radicals: $C_{11}H_{23}$, $C_{13}H_{27}$, radicals derived from copra fatty acids, radical derived from oleic acid.

The compounds prepared by alkali-catalysed condensation of 3.5 moles of glycidol with a mixture of alphadiols containing from 11 to 14 carbon atoms according to French Pat. No. 2,091,516 or U.S. Pat. No. 3,821,372 are particularly preferred.

In the dentifrice compositions according to the invention:

the poly(hydroxypropyl ether) surfactant or compound A is present in proportions of 0.1 to 4% and preferably of 0.2 to 2% by weight based on the total weight of the composition;

an anionic surfactant which is a salt of a specific derivative of a protein degradation product, or compound B, is present in proportions of 0.1 to 4% and preferably of 0.2 to 2% by weight based on the total weight of the composition.

The ratio A/B by weight is between 0.2 and 0.5, preferably between 0.5 and 2, and advantageously between 0.9 and 1.1.

In the present description, "surfactant" is synonymous with "surface agent".

The dentifrices according to the invention generally contain one or more abrasive polishing agents which are predominantly insoluble in water.

Among these polishing agents there may be mentioned by way of example sodium or potassium metaphosphates, tricalcium phosphate, calcium phosphate dihydrate, dicalcium phosphate, calcium pyrophosphate, calcium carbonate, alumina, alumina hydrates and especially alumina trihydrates, silica, aluminium or zirconium silicates, bentonite, as well as magnesium orthophosphate or trimagnesium phosphate.

In the case of transparent gels, a polishing agent based on colloidal silica or on complex alkali metal aluminosilicates will preferably be employed.

The abrasive polishing agent represents 10 to 80% and preferably 15 to 65% of the total weight of the composition.

The dentifrice according to the invention may also contain one or more bactericidal agents intended to combat the formation of dental plaque. These bactericidal agents are generally cationic nitrogen compounds. Among these cationic compounds there may be mentioned by way of example:
diisobutylphenoxyethoxyethyldimethylbenzylammonium chloride,
dodecyltrimethylammonium bromide,
dodecyldimethyl(2-phenoxyethyl)ammonium bromide,
benzyldimethylstearylammonium chloride,
cetylpyridinium chloride,
quaternized 5-amino-1,3-bis(2-ethylhexyl)-5-methylhexahydroxypyrimidine,
trimethylcetylammonium bromide,
alkyldimethylhydroxyethylammonium bromide (where alkyl denotes a mixture of radicals derived from copra fatty acids),
chlorhexidine,
alexidine, and
cationic tertiary aliphatic amines.

These bactericidal agents are generally present at between 0.005 and 10% and preferably between 0.05 and 2% by weight based on the total weight of the composition.

The dentifrice according to the invention also contains water or a humectant in a proportion of 10 to 80% of the total weight of the composition. This humectant is advantageously chosen from the group consisting of glycerine, sorbitol, propylene glycol, and polyethylene glycols of low molecular weights, such as polyethylene glycols 400 and 2,000.

The dentifrice may also contain cohesion agents. These are generally natural resins or synthetic thickeners.

Gum tragacanth, xanthan gums, guar gums, carob gums and carragheen gums may be mentioned as natural resins.

The synthetic thickeners which are employed are essentially cellulose derivatives such as the sodium salt of carboxymethyl cellulose, methyl cellulose or hydroxyalkyl celluloses.

These cohesion agents may be present in a proportion by weight which varies between 0.1 and 10%, and preferably between 0.2 and 3%.

The dentifrice according to the invention generally contains a sweetening agent in a concentration which generally varies between 0.1 and 2% based on the total weight of the dentifrice. Among the sweetening agents there may be mentioned, by way of example: sucrose, lactose, fructose, xylitol, sodium cyclamate, maltose and sodium saccharinate.

The dentifrice according to the invention may also contain a preservative in a quantity which is generally between 0.01 and 0.5% based on the total weight of the dentifrice. Among the preservatives there may be mentioned, by way of example, compounds such as formaldehyde and its derivatives, methyl parahydroxybenzoate, propyl para-hydroxybenzoate, and the like.

The dentifrice according to the invention may contain a flavouring substance in a proportion of between 0.5 and 5% by weight based on the total weight of the dentifrice. Among the flavouring substances, the following may be mentioned by way of example: essences of mint (spear or pepper), aniseed, eucalyptus, cinnamon, clove, sage, liquorice, essences of fruits such as lemon, orange, mandarine and strawberry, or, if desired, methyl salicylate.

The pH of the dentifrice according to the invention is usually between 4.5 and 9, and preferably between 5.5 and 8.5. It is measured conventionally for a 20% dispersion of dentifrice in water.

Acidifying agents must generally be added. Among these, citric acid, benzoic acid, monosodium phosphate and disodium phosphate may be mentioned by way of example.

In general, alkaline pH values are employed only in the case of dentifrices containing a compound which is unstable in a neutral or acidic medium as a polishing agent. This is the case, for example, with dentifrices containing calcium carbonate as a polishing agent.

The dentifrice according to the invention advantageously contains an anticaries agent. These are carriers of fluoride ions. Among these, the following soluble inorganic fluorides may be mentioned by way of example: sodium, potassium, calcium, ammonium, zinc, tin, copper and barium fluorides, sodium or ammonium fluorosilicate, sodium or aluminium monofluorophosphate, aluminium difluorophosphate and sodium fluorozirconate. The most commonly employed fluorine compounds are sodium fluoride, sodium monofluorophosphate and mixtures thereof.

The fluorine ion carrier is employed at a concentration such that the fluoride ion content does not exceed 1,500 ppm. By way of example, the concentrations employed are, in the case of sodium fluoride, between 0.05 and 0.25% and, in the case of sodium monofluorophosphate, these concentrations vary from 0.2 to 0.8% by weight of the total weight.

The dentifrice according to the invention may also contain other adjuvants which are usually employed in compositions for tooth, gum and mouth care.

The examples which follow illustrate the invention without, however, limiting it.

EXAMPLE 1

The following dentifrice is prepared:
Nonionic poly(hydroxypropyl ether) surfactant prepared by alkali-catalysed condensation of 3.5 moles of glycidol with a mixture of alpha-diols containing from 11 to 14 carbon atoms according to the process described in French Pat. No. 2,091,516 or in U.S. Pat. No. 3,821,372: 1.00 g AS (AS=active substance)
Sodium lauroylsarcosinate sold by the Ciba-Geigy company under the name Sarkosyl NL 97: 1.00 g
Syloid AL1*: 8.50 g
Syloid 244*: 11.05 g
Sodium carboxymethyl cellulose sold by the Hercules company under the name CMC 9M 31F: 0.34 g
Polyethylene glycol PEG 2000 sold by the Hoechst company: 2.00 g
Sodium saccharinate: 0.15 g
Anhydrous disodium phosphate: 0.045 g
Sorbitol as 70% strength aqueous solution: 65.00 g
Flavour, colorant, preservative: q.s.
Natural pH: 6.3
Water: q.s. 100.00 g
*Syloid: silicas sold by the Grace company.

This dentifrice has good foamability and leaves no bitterness in the mouth.

EXAMPLE 2

The following dentifrice is prepared:
Nonionic poly(hydroxypropyl ether) surfactant prepared by alkali-catalysed condensation of 3.5 moles of glycidol with a mixture of alpha-diols containing from 11 to 14 carbon atoms, according to the process described in French Pat. No. 2,091,516 or in U.S. Pat. No. 3,821,372: 1.00 g AS
Potassium salt of the condensate of copra fatty acids with a hydrolysed animal protein, sold at a concentration of 30% of AS by the Grunau company under the name Lamepon S: 1.00 g AS
Syloid AL1*: 8.50 g
Syloid 244*: 11.05 g
Sodium carboxymethyl cellulose sold by the Hercules company under the name CMC 9M 31F: 0.34 g
Polyethylene glycol PEG 2000 sold by the Hoechst company: 2.00 g
Sodium saccharinate: 0.15 g
Anhydrous disodium phosphate: 0.045 g
Anhydrous trisodium phosphate: 0.0425 g
Sorbitol as 70% strength aqueous solution: 65.00 g
Flavour, colorant, preservative: q.s.
Natural pH: 6.4
Water: q.s. 100.00 g
*Syloid: silicas sold by the Grace company.

This dentifrice has good foamability and leaves no bitterness in the mouth.

EXAMPLE 3

A dentifrice gel of the following composition is prepared:
Nonionic surfactant of formula:

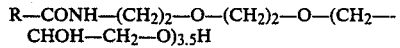

where R denotes the following mixture of alkyl and alkenyl radicals (% by weight):
35% $C_{12}H_{25}$-15% $C_{14}H_{29}$-15% oleyl radicals-35% radicals derived from copra fatty acids: 1.15 g AS
Sodium lauroylsarcosinate sold at a concentration of 30% AS by the Seppic company under the name Oramix L30: 1.23 g AS
Silica sold by the Grace company under the name Syloblanc 94: 8.5 g
Silica sold by the Grace company under the name Syloblanc 34: 11.05 g
Sodium carboxymethyl cellulose sold by the Hercules company under the name CMC 9M 31F: 0.34 g
Polyethylene glycol PEG 2000 sold by the Hoechst company: 2 g
Sorbitol as 70% strength aqueous solution: 65 g
Sodium saccharinate: 0.15 g
Anhydrous disodium phosphate: 0.045 g
Colorant, preservative, flavour: q.s.
Natural pH: 6.8
Water: q.s. 100 g

EXAMPLE 4

A dentifrice gel of the following composition is prepared:
Nonionic surfactant of formula:

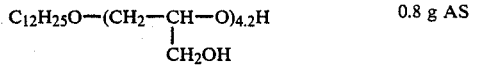

0.8 g AS

Potassium salt of the condensate of copra fatty acids with a hydrolysed animal protein sold at a concentration of 30% AS by the Grunau company under the name Lamepon S: 0.73 g AS
Silica sold by the Grace company under the name Syloblanc 94: 8.5 g
Silica sold by the Grace company under the name Syloblanc 34: 11.05 g
Sodium carboxymethyl cellulose sold by the Hercules company under the name CMC 9M 31F: 0.34 g
Polyethylene glycol PEG 2000 sold by the Hoechst company: 2 g
Sorbitol as 70% strength aqueous solution: 65 g
Sodium saccharinate: 0.15 g
Anhydrous disodium phosphate: 0.045 g
Colorant, preservative, flavour: q.s.
Natural pH: 6.7
Water: q.s. 100 g

I claim:

1. Dentifrice comprising:
   (A) a poly(hydroxypropyl ether) nonionic surfactant present in proportions of 0.1 to 4% by weight based on the total weight of the composition, and
   (B) an anionic surfactant present in proportions of 0.1 to 4% by weight based on the total weight of the composition which is a salt of a specific derivative of a protein degradation product selected from the group consisting of:
   (i) a salt of an N-acyl-N-methylglycine (N-acylsarcosine) of formula:

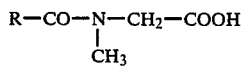

where R denotes an alkyl radical or a mixture of alkyl radicals containing from 9 to 17 carbon atoms, and
   (ii) a salt of a condensate of $C_{12}$-$C_{18}$ fatty acids with a hydrolysed animal protein.

2. Dentifrice according to claim 1, wherein the anionic surfactant, the salt of a specific derivative of a protein degradation product, is sodium N-lauroylsarcosinate.

3. Dentifrice according to claim 1, wherein the anionic surfactant, the salt of a specific derivative of a protein degradation product, is the potassium salt of a condensate of copra fatty acids with a hydrolysed animal protein.

4. Dentifrice according to claim 1, wherein the poly(hydroxypropyl ether) nonionic surface agent is selected from the group consisting of:
   (1) the compounds of formula (I):

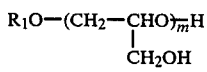 (I)

where $R_1$ denotes a radical or a mixture of alkyl radicals containing 10 to 14 carbon atoms and m is an integer or decimal from 2 to 10 and preferably from 3 to 6;
   (2) the compounds of formula (II):

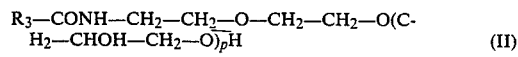 (II)

where $R_3$ denotes a radical or a mixture of alkyl and/or alkenyl radicals containing from 11 to 17 carbon atoms and p denotes an integer or decimal from 1 to 5 and preferably from 1.5 to 4;
   (3) the compounds prepared by alkali-catalysed condensation of 2 to 10 moles and preferably of 2.5 to 6 moles of glycidol with an alpha-diol or a mixture of $C_{10}$-$C_{14}$ alpha-diols;
   (4) the compounds prepared by acid-catalysed condensation of 2 to 10 and preferably of 2.5 to 6 moles of glycidol per mole of alcohol or of alpha-diol containing 10 to 14 carbon atoms.

5. Dentifrice according to claim 4, wherein the poly(hydroxypropyl ether) surfactant is selected from the group consisting of the compounds of formulae:

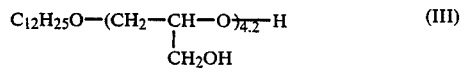 (III)

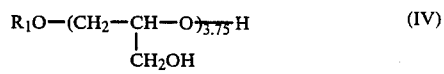 (IV)

where $R_1$ denotes a mixture of $C_{10}$ and $C_{12}$ alkyl radicals.

6. Dentifrice according to claim 4, wherein the poly(hydroxypropyl ether) surfactant is the compound:

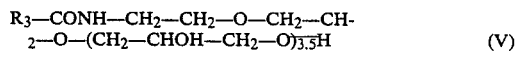 (V)

where $R_3$ denotes a mixture of radicals comprising the following alkyl and alkenyl radicals:
   $C_{11}H_{23}$, $C_{13}H_{27}$, radicals derived from copra fatty acids, radical derived from oleic acid.

7. Dentifrice according to claim 4, wherein the poly(hydroxypropyl ether) surfactant is prepared by alkali-catalysed condensation of 3.5 moles of glycidol with a mixture of alpha-diols containing from 11 to 14 carbon atoms.

8. Dentifrice according to claim 1, wherein the ratio A/B by weight is between 0.2 and 5.

9. Dentifrice according to claim 8, wherein the ratio A/B by weight is between 0.9 and 1.1.

10. Dentifrice according to claim 1, containing 10 to 80% by weight of a polishing agent.

11. Dentifrice according to claim 1, containing from 0.005 to 10% by weight of an antiplaque bactericidal agent.

12. Dentifrice according claim 1, also containing a carrier of fluorine ions corresponding to a fluorine ion content not exceeding 1,500 ppm.

13. Dentifrice according to claim 1, also containing ingredients selected from the group consisting of humectants, cohesion agents, sweetening agents, preservatives and flavouring substances.

* * * * *